(12) United States Patent
Lee et al.

(10) Patent No.: US 10,125,181 B2
(45) Date of Patent: Nov. 13, 2018

(54) THERMOSTABLE HUMAN EPIDERMAL GROWTH FACTOR-SPIDER VENOM FUSION PROTEIN WITH INCREASED SKIN CELL PROLIFERATION EFFECT AND COSMETIC COMPOSITION FOR ANTI-WRINKLE AND MAINTAINING ELASTICITY OF SKIN COMPRISING THE SAME AS EFFECTIVE COMPONENT

(71) Applicants: NEXGEN BIOTECHNOLOGIES, INC., Seoul (KR); Sun Kyo Lee, Gyeonggi-do (KR)

(72) Inventors: Sun Kyo Lee, Gyeonggi-do (KR); Han Bong Ryu, Seoul (KR); Seong Ran Lee, Gyeonggi-do (KR); Jong Nam Choi, Gyeonggi-do (KR); Tae Hyun Kim, Gyeonggi-do (KR); Tae Won Choi, Seoul (KR); Tae Hwa Jeong, Gyeonggi-do (KR); Hyeong Il Kwon, Seoul (KR)

(73) Assignees: NEXGEN BIOTECHNOLOGIES, INC, Seoul (KR); Sun Kyo Lee, Gyeonggi-Do (KR)

( * ) Notice: Subject to any disclaimer, the term of this patent is extended or adjusted under 35 U.S.C. 154(b) by 0 days.

(21) Appl. No.: 15/522,159

(22) PCT Filed: Jul. 22, 2016

(86) PCT No.: PCT/KR2016/007984
§ 371 (c)(1),
(2) Date: Apr. 26, 2017

(87) PCT Pub. No.: WO2017/209347
PCT Pub. Date: Dec. 7, 2017

(65) Prior Publication Data
US 2018/0186848 A1    Jul. 5, 2018

(30) Foreign Application Priority Data

Jun. 3, 2016  (KR) .......................... 10-2016-0069272

(51) Int. Cl.
*A61K 8/64* (2006.01)
*A61Q 19/00* (2006.01)
*A61Q 19/08* (2006.01)
*C12N 15/62* (2006.01)
*C07K 14/435* (2006.01)
*C07K 14/485* (2006.01)

(52) U.S. Cl.
CPC .............. *C07K 14/485* (2013.01); *A61K 8/64* (2013.01); *A61Q 19/00* (2013.01); *A61Q 19/08* (2013.01); *C07K 14/435* (2013.01); *C07K 14/43518* (2013.01); *C12N 15/62* (2013.01)

(58) Field of Classification Search
None
See application file for complete search history.

(56) References Cited

FOREIGN PATENT DOCUMENTS

| KR | 10-2005-0027838 A | 3/2005 |
|---|---|---|
| KR | 10-2015-0056022 A | 5/2015 |
| KR | 10-1613302 B1 | 4/2016 |

OTHER PUBLICATIONS

Bowie et al. (Science, 1990, 247:1306-1310) (Year: 1990).*
Snapp (Curr Protoc Cell Biol. Jul. 2005 ; Chapter: Unit-21.4) (Year: 2005).*
Booth et al (ACS Omega 2018, 3, 760-768) (Year: 2018).*
Hanahan, Douglas, "Studies on Transformation of *Escherichia coil* with Plasmids", J. Mol. Biol. vol. 166, pp. 557-580, 1983.
F.S. Torres et al., "Functional expression of a recombinant toxin—rPnTx2-6—active in erectile function in rat", Toxicon, vol. 56. pp. 1172-1180, 2010.
Yang, Xiaoping et al.,"Diphtheria Toxin—Epidermal Growth Factor Fusion Protein DAB389EGF for the Treatment of Bladder Cancer", Cancer Therapy: Preclinical, Clin Cancer Res; vol. 19, No. 1, pp. 148-157, 2013.
Chandramohan, Vidyalakshmi et al., "Toxin-Based Targeted Therapy for Malignant Brain Tumors", Clinical and Developmental Immunology, vol. 2012, Article ID 480429, Intenal pp. 1-15, 2012.
Thakur, Mayank et al., "Targeted tumor therapy by epidermal growth factor appended toxin and purified saponin: An evaluation of toxicity and therapeutic potential in syngeneic tumor bearing mice", Molecular Oncology, vol. 7, pp. 175-483, 2013.
NCBI GenBank,"listeriolysin O/epidermal growth factor fusion protein, partial [synthetic construct]", Access No. AJF94343.1, Feb. 2015.

* cited by examiner

*Primary Examiner* — Brian Gangle
*Assistant Examiner* — Andrea K McCollum
(74) *Attorney, Agent, or Firm* — The PL Law Group, PLLC

(57) ABSTRACT

A thermostable human epidermal growth factor-spider venom fusion protein with increased skin cell proliferation effect has the amino acid sequence of SEQ ID NO: 2, a gene of *E. coli* codon-optimized nucleotide sequence of SEQ ID NO: 1 for encoding the human epidermal growth factor-spider venom fusion protein, a recombinant vector including the gene, a host cell transformed with the recombinant vector, and a method for producing in a host cell a human epidermal growth factor-spider venom fusion protein by transforming a host cell with the recombinant vector, and a cosmetic composition for improving skin wrinkle and maintaining skin elasticity including a human epidermal growth factor-spider venom fusion protein, and as the cosmetic composition has excellent thermostability and has an effect of enhancing the activity of improving skin wrinkle and maintaining skin elasticity, it can be advantageously used in future in the field of cosmetics or cosmetic plastic surgery.

12 Claims, 8 Drawing Sheets

Figure 2A:
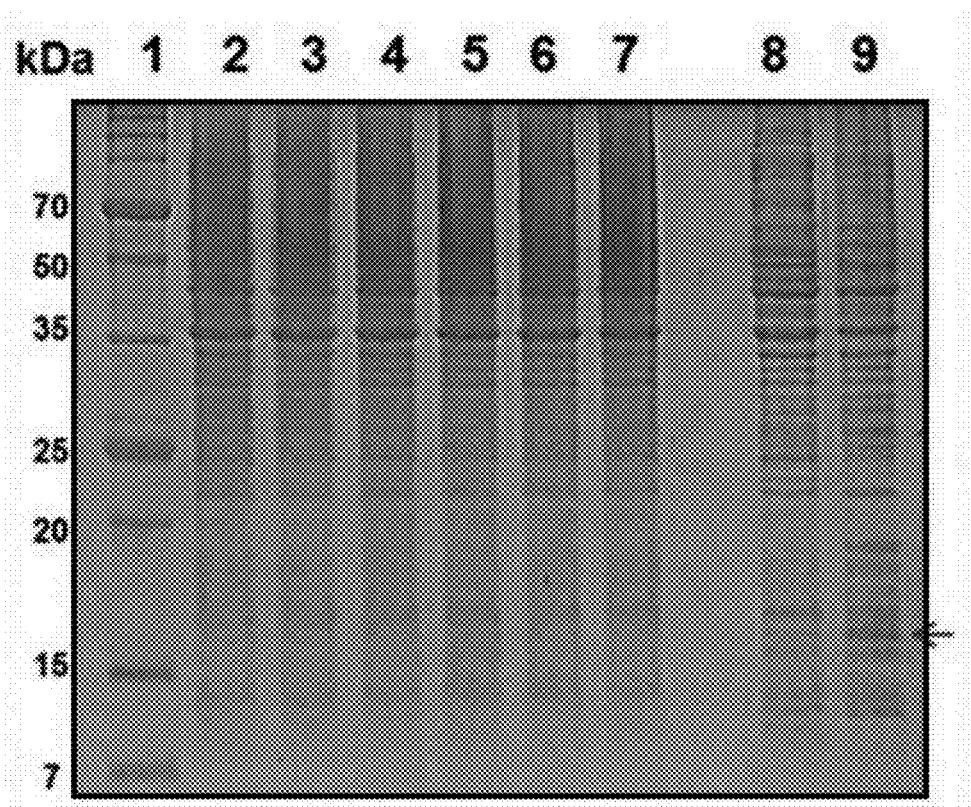

Specification includes a Sequence Listing.

Fig. 1

Human epidermal growth factor-spider venom fusion protein expression scheme

Forward primer →
[EGF domain] [SV domain]
← Reverse primer

⇓

Gene synthesis

[EGF domain] [SV domain]

pET22b vector ⇘  ⇙ Ligation

Transformation (*E. coli* TOP10)

[EGF domain] [SV domain]
pET22b::ESV

⇓

Transformation
(*E. coli* Rosetta2 pLysS)

⇓

Recombinant microorganism expressing human epidermal growth factor
-spider venom fusion protein

THERMOSTABLE HUMAN EPIDERMAL GROWTH FACTOR-SPIDER VENOM FUSION PROTEIN WITH INCREASED SKIN CELL PROLIFERATION EFFECT AND COSMETIC COMPOSITION FOR ANTI-WRINKLE AND MAINTAINING ELASTICITY OF SKIN COMPRISING THE SAME AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/007984, filed Jul. 22, 2016, which claims priority to the benefit of Korean Patent Application No. 10-2016-0069272 filed in the Korean Intellectual Property Office on Jun. 3, 2016, the entire contents of which are incorporated herein by reference.

TECHNICAL FIELD

The present invention relates to a thermostable human epidermal growth factor-spider venom fusion protein with increased skin cell proliferation effect and a cosmetic composition for improving skin wrinkle and maintaining elasticity of skin comprising the same as effective component.

BACKGROUND ART

Skin is composed of epidermis, dermis, and subcutaneous tissue. While providing protection against an attack by microbes that are introduced form an outside, skin plays a very important role for maintaining body moisture and body temperature. Epidermis plays a role of protecting skin, regulating body temperature, and maintaining body moisture, and it is composed of an extracellular matrix which is related to skin elasticity and skin flexibility. Dermis is directly related with skin aging.

Upon binding to a receptor for an epidermal growth factor present on a surface of a cell, the human epidermal growth factor (hEGF) induces a dimerization of a receptor for an epidermal growth factor. A dimeric receptor for an epidermal growth factor activates the tyrosine kinase present in the receptor to induce an intracellular signal transduction system. As a result of those processes, glycolysis and protein synthesis are promoted in a cell, eventually leading to cell growth.

The epidermal growth factor playing an important role in skin regeneration decreases according to a progress of aging, and a decrease in the epidermal growth factor causes a reduction in skin cell proliferation and transfer, and thus phenomena like skin aging, increased wrinkles, and reduced skin elasticity are exhibited accordingly.

PnTx2-6 as one spider venom of a Brazilian wandering spider (*Phoneutria nigriventer*) is composed of 403 nucleotides which consist of many glutamates and signal peptides. PnTx2-6 is known to have an influence on a flux through a sodium ion channel and induce an erection in an anesthetized rat.

As a spider venom of a Brazilian wandering spider, 100 or more kinds of a polypeptide with a size of 3,500 to 9,000 Da are known. By inducing secretion of acetylcholine and glutamate in TTX (tetrodotoxin)-sensitive way, it increases the introduction of sodium ions into a cortical synaptosome, thus preventing inactivation of a sodium channel. Accordingly, a phenomenon of priapism is caused.

As one of the spider venoms of a Brazilian wandering spider which cause a phenomenon of priapism, PnTx2-6 has been continuously studied all over the world since 2010 as a natural protein which may be used as a substitute for Viagra. However, the accurate intracellular working mechanism of PnTx2-6 is not known yet, and there are only few studies that are known to be related to a large scale production of PnTx2-6 for its use as a natural protein which can substitute Viagra.

Meanwhile, in Korean Patent Registration No. 1613302, "SV82 polypeptide and a cosmetic composition for improving skin wrinkle and maintaining skin elasticity comprising the same as effective component" is disclosed. Furthermore, in Korean Patent Application Publication No. 2015-0056022, a "cosmetic composition for improving skin comprising fusion protein of epidermal grown factor" is disclosed. However, no description has been made for the thermostable human epidermal growth factor-spider venom fusion protein with increased skin cell proliferation effect and cosmetic composition for improving skin wrinkle and maintaining elasticity of skin comprising the same as effective component of the present invention.

SUMMARY

The present invention is devised in view of the circumstances described above, and according to fusion of human epidermal growth factor to a spider venom protein, the inventors of the present invention produced a novel thermostable human epidermal growth factor-spider venom fusion protein with increased skin cell proliferation effect. The human epidermal growth factor-spider venom fusion protein can not only promote skin cell proliferation but also has very excellent thermostability. Thus, as a result of producing various cosmetic formulations (e.g., skin, essence, lotion, and crème) containing the human epidermal growth factor-spider venom fusion protein as an effective component and carrying out a skin test, the effect of improving skin wrinkle and maintaining skin elasticity was confirmed with a test subject. The present invention is completed accordingly.

To solve the problems described above, the present invention provides a thermostable human epidermal growth factor-spider venom fusion protein with increased skin cell proliferation effect which consists of the amino acid sequence of SEQ ID NO: 2.

The present invention also provides a gene encoding the aforementioned fusion protein.

The present invention also provides a recombinant vector comprising the aforementioned gene.

The present invention also provides a host cell transformed with the aforementioned recombinant vector.

The present invention also provides a method for producing in a host cell a human epidermal growth factor-spider venom fusion protein comprising overexpressing a gene encoding a human epidermal growth factor-spider venom fusion protein by transforming a host cell with the aforementioned recombinant vector.

The resent invention also provides a cosmetic composition for improving skin wrinkle and maintaining skin elasticity comprising, as an effective component, a human epidermal growth factor-spider venom fusion protein which consists of the amino acid sequence of SEQ ID NO: 2.

The method of production in *E. coli* using *E. coli* codon-optimized gene encoding human epidermal growth factor-spider venom fusion protein of the present invention has a simplified production step as proteins are expressed in the form of an inclusion body in E. coli (Escherichia coli) and allows large scale production of proteins Furthermore, as the human epidermal growth factor-spider venom fusion protein produced by the aforementioned method has thermostability and an excellent function of improving skin wrinkle and maintaining skin elasticity, it is expected that the fusion protein is advantageously used as a raw material of functional cosmetics.

BRIEF DESCRIPTION OF THE DRAWINGS

FIG. 1 is a schematic drawing illustrating the process for preparing the recombinant plasmid (pET22b::ESV) which includes a gene encoding the human epidermal growth factor-spider venom fusion protein (ESV), and transforming *E. coli* with the plasmid.

FIGS. 2A to 2C show the results of *E. coli* expression and determination by separation of the human epidermal growth factor-spider venom fusion protein (i.e., human epidermal growth factor-spider venom fusion protein having the human epidermal growth factor fused the amino terminal of spider venom protein; ESV). FIG. 2A shows the results of SDS-polyacrylamide gel electrophoresis which has been carried out to determine the presence or absence of the expression: 1; size marker, 2 to 4; crude cell lysate before expression induction, 5 to 7; crude cell lysate after expression induction, 8; total water soluble proteins after expression induction, 9; total insoluble proteins (i.e., inclusion body) after expression induction, and arrow; expected ESV. FIG. 2B shows the results of SDS-polyacrylamide gel electrophoresis of the human epidermal growth factor-spider venom fusion protein which has been finally separated by using nickel agarose column. FIG. 2C shows the result of determining the human epidermal growth factor domain by using an EGF detection kit in which the determination was made to examine the human epidermal growth factor domain of the finally separated human epidermal growth factor-spider venom fusion protein. In FIG. 2C, C represents EGF control and T represents a test sample.

FIG. 3 is a photographic image in which the dermal fibroblast proliferation effect after the treatment of dermal fibroblast with the human epidermal growth factor-spider venom fusion protein (ESV) is shown by crystal violet staining.

FIG. 4 is a photographic image in which the presence or absence of dermal fibroblast proliferation after the treatment of dermal fibroblast with the human epidermal growth factor-spider venom fusion protein (ESV), which has been subjected to either gamma sterilization or high pressure sterilization, is shown for determination of thermal stability of the fusion protein, in which the dermal fibroblast cell proliferation was determined by crystal violet staining.

FIG. 5 is a graph illustrating the result of the HaCaT cell proliferation effect after treatment of HaCaT cells with human epidermal growth factor-spider venom fusion protein (ESV).

FIG. 6 is a photographic image showing the wound healing effect in HaCaT cells after treatment of HaCaT cells with human epidermal growth factor-spider venom fusion protein (ESV).

FIG. 7 is a graph showing the fusion between HaCaT cells and the human epidermal growth factor-spider venom fusion protein after treating HaCaT cells in a multi-well coated with the human epidermal growth factor-spider venom fusion protein (ESV).

DETAILED DESCRIPTION

To achieve the object of the present invention, the present invention provides a thermostable human epidermal growth factor-spider venom fusion protein with increased skin cell proliferation effect which consists of the amino acid sequence of SEQ ID NO: 2.

The scope of the human epidermal growth factor-spider venom fusion protein according to the present invention includes a protein having an amino acid sequence represented by SEQ ID NO: 2, and also functional equivalents of the protein. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it indicates a protein exhibiting substantially the same physiological activity as the protein represented by SEQ ID NO: 2. The expression "substantially the same physiological activity" means an activity of improving skin wrinkle and maintaining skin elasticity. Furthermore, included in the human epidermal growth factor-spider venom fusion protein are a fragment, a derivative, and an analogue thereof. The terms "fragment", "derivative", and "analogue" that are used herein indicate a polypeptide which has substantially the same physiological function or activity as the human epidermal growth factor-spider venom fusion protein of the present invention.

The human epidermal growth factor-spider venom fusion protein of the present invention preferably consists of 103 amino acids of SEQ ID NO: 2, and it may be a novel protein which is produced by fusion between the human epidermal growth factor consisting of the $1^{st}$ to the $53^{rd}$ amino acids and the spider venom protein consisting of the $54^{th}$ to the $103^{rd}$ amino acids of the above amino acid sequence.

The present invention further provides a gene encoding the thermostable human epidermal growth factor-spider venom fusion protein with increased skin cell proliferation effect. This gene may consist of a nucleotide sequence of *E. coli* codon-optimized SEQ ID NO: 1, but not limited thereto.

The gene encoding the thermostable human epidermal growth factor-spider venom fusion protein with increased skin cell proliferation effect of the present invention may include a nucleotide sequence of SEQ ID NO: 1. Further, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence of SEQ ID NO: 1. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

"Codon optimization" means a modification of codon of a polynucleotide encoding a protein with a codon that is used first than others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism. The nucleotide sequence of SEQ ID NO: 1 of the present invention is a sequence which has been optimized to *E. coli* codon such that the gene encoding the human epidermal growth factor-spider venom fusion protein can be expressed well in *E. coli*.

The present invention also provides a recombinant vector comprising the gene described above, and a host cell transformed with the recombinant vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding human epidermal growth factor-spider venom fusion protein can be inserted to a recombinant expression vector. The term "recombinant expression vector" means bacteria plasmid, phage, yeast plasmid, plant cell virus, mammalian cell virus, or other vector. Any plasmid and vector can be generally used if it can replicate and is stabilized in a host. Important characteristics of the expression vector include that it comprises a replication origin, a promoter, a marker gene, and a translation control element.

The expression vector comprising the gene sequence encoding the human epidermal growth factor-spider venom fusion protein and an appropriate signal for regulating transcription/translation can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

The recombinant vector according to one embodiment of the present invention is prepared by in-frame fusion of 5' terminal (NdeI restriction enzyme site) and 3' terminal (XhoI restriction enzyme site) of the gene encoding the human epidermal growth factor-spider venom fusion protein (SEQ ID NO: 1) to pET22b vector, and it is a vector characterized in that it can produce the human epidermal growth factor-spider venom fusion protein based on effective expression of the aforementioned gene with an aid of lac promoter (lac promoter) and lacI repressor (lacI repressor).

For a host cell having an ability of having stable and continuous cloning and expression of the vector of the present invention, any host cell known in the pertinent art can be used. Examples of the prokaryotic cells include, *Bacillus* sp. strain including *E. coli* ROSETTA, *E. coli* JM109, *E. coli* BL21, *E. coli* RR1, *E. coli* LE392, *E. coli* B, *E. coli* X 1776, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

Furthermore, when an eukaryotic cell is transformed with the vector of the present invention, yeast (*Saccharomyces cerevisiae*), an insect cell, a human cell (for example, CHO (Chinese hamster ovary) cell line, W138, BHK, COS-7, 293, HepG2, 3T3, RIN, and MDCK cell line), a plant cell, and the like can be used as a host cell.

The host cell transformed with the recombinant vector according to one embodiment of the present invention can be *E. coli* ROSETTA2 (DE3) pLysS, but not limited thereto.

When a host cell is a prokaryotic cell, delivery of the recombinant vector of the present invention into a host cell can be carried out by $CaCl_2$ method, Hanahan's method (Hanahan, D., J. Mol. Biol., 166:557-580 (1983)) or an electroporation method, and the like. In addition, when a host cell is an eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method for producing in a host cell a human epidermal growth factor-spider venom fusion protein comprising overexpressing a gene encoding a human epidermal growth factor-spider venom fusion protein by transforming a host cell with the recombinant vector described above.

With regard to the method according to one embodiment of the present invention, the host cell can be preferably *E. coli*, and more preferably *E. coli* ROSETTA2 (DE3) pLysS, but not limited thereto.

The present invention still further provides a cosmetic composition for improving skin wrinkle and maintaining skin elasticity comprising, as an effective component, a human epidermal growth factor-spider venom fusion protein which consists of the amino acid sequence of SEQ ID NO: 2.

In the cosmetic composition according to one embodiment of the present invention, content of the human epidermal growth factor-spider venom fusion protein may be 0.000001 to 0.02% by weight relative to the total weight of the cosmetic composition, but not limited thereto.

In the cosmetic composition of the present invention, components that are typically used for a cosmetic composition are included in addition to the effective components that are described above. Examples thereof include a lipid material, an organic solvent, a dissolution agent, a condensation agent, a gelling agent, a softening agent, an antioxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or liphophilic activating agent, a common auxiliary agent such as lipid vesicle, and a carrier.

The composition of the present invention can be prepared in any formulation which is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but not limited thereto. More specifically, the composition may be formulated into a skin, a skin softener, a skin toner, an astringent, a lotion, a milk lotion, a moisture lotion, a nutrition lotion, a massage crème, an eye crème, a moisture crème, a hand crème, an essence, a nutrition essence, a pack, a cleansing foam, a cleansing water, a cleansing lotion, a cleansing crème, a body lotion, a body cleanser, a soap, a powder, or the like.

In a case in which the cosmetic composition of the present invention has a formulation type of paste, crème, or gel, it is possible to use, as a carrier component, animal oil, plant oil, wax, paraffin, starch, tragacanth, cellulose derivatives, polyethylene glycol, silicone, bentonite, silica, talc, or zinc oxide.

In a case in which the cosmetic composition of the present invention has a formulation type of powder or spray, it is possible to use, as a carrier component, lactose, talc, silica, aluminum hydroxide, calcium silicate, or polyamide powder. In particular, in a case in which the cosmetic composition is a spray, a propellant such as chlorofluorohydrocarbon, propane/butane, or dimethyl ether may be additionally included.

In a case in which the cosmetic composition of the present invention has a formulation type of solution or emulsion, a solvent, a dissolution agent, or an emulsifier is used as a carrier component, and examples thereof include isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethlyene sorbitol ester, or polyoxyethylene sorbitan ester, microcrystalline cellulose, aluminum metahydroxide, bentonite, agar, or tragacanth.

Hereinbelow, the present invention is explained in greater detail in view of the Examples. However, it is evident that the following Examples are given only for exemplification of the present invention and by no means the present invention is limited to the following Examples.

EXAMPLES

Example 1. Preparation of Recombinant Expression Vector and Transformed Recombinant Microorganism for Producing Human Epidermal Growth Factor-Spider Venom Fusion Protein The optimized gene encoding the human epidermal growth factor-spider venom fusion protein, recombinant expression vector, and transformed recombinant microorganism were prepared in accordance with the following methods.

By using as a template the genes encoding the spider venom protein or human epidermal growth factor used as a partner protein, the gene (SEQ ID NO: 1) fragment encoding the human epidermal growth factor-spider venom fusion protein which consists of 103 amino acids and has been optimized for expression in a host microorganism was prepared and synthesized.

To synthesize the gene encoding the human epidermal growth factor-spider venom fusion protein (SEQ ID NO: 2) having the spider venom protein bound to the carboxy terminal (C-terminal) of human epidermal growth factor, 159 bp nucleotide (i.e., $1^{st}$ to $159^{th}$ nucleotides of SEQ ID NO: 1) encoding the human epidermal growth factor, which has been optimized for $E.\ coli$, was synthesized by using a forward primer 1 (5'-AAGGAGATATACATATGAACTCA-GAC-3', SEQ ID NO: 3) and a reverse primer 1 (5'-AGCCCTGGCGCGCAACTC-3', SEQ ID NO: 4). Furthermore, 150 bp nucleotide (i.e., $160^{th}$ to $309^{th}$ nucleotides of SEQ ID NO: 1) encoding the spider venom protein, which has been optimized for $E.\ coli$, was synthesized by using a forward primer 2 (5'-GAGTTGCGCGCCAGGGCT-3', SEQ ID NO: 5) and a reverse primer 2 (5'-GTGCTC-GAGTTTCTTGCA-3', SEQ ID NO: 6)

By having each of the genes encoding the human epidermal growth factor or spider venom protein, which have been synthesized by the above method, as a template and also by using a forward primer 1 (SEQ ID NO: 3) and a reverse primer 2 (SEQ ID NO: 6), a gene consisting of 309 nucleotides encoding a fusion protein in which the spider venom protein is bound to the C-terminal of the human epidermal growth factor was finally obtained by polymerase chain reaction (PCR).

The aforementioned gene fragment and recombinant plasmid were digested with the same restriction enzymes (5' terminal NdeI and 3' terminal XhoI) followed by insertion, and thus the recombinant plasmid (pET22b::ESV) shown in FIG. 1 was prepared. Then, $E.\ coli$ TOP10 was transformed with the prepared recombinant plasmid to obtain a large amount of the gene construct from the host microorganism.

After that, $E.\ coli$ ROSETTA2 (DE3) pLysS (NOVAGEN, Germany) was transformed with the prepared recombinant plasmid to produce a recombinant microorganism for producing a human epidermal growth factor-spider venom fusion protein.

Example 2. Expression Induction, Isolation, and Purification of Human Epidermal Growth Factor-Spider Venom Fusion Protein $E.\ coli$ ROSETTA2 (DE3) pLysS prepared in Example 1 was cultured in 1 L LB medium (10% tryptophan, 10% sodium chloride, and 5% yeast extract) or BSB medium (1% tryptophan, 0.5% yeast extract, 1% glucose, and 0.1% HEPES (pH 7.0), manufactured by Nexgen Biotechnologies, Inc.) till to have $OD_{600}$=0.6 to 0.8 for batch culture, or $OD_{600}$=15 to 20 for continuous culture using 20 L fermentation apparatus. After that, by adding 1 to 5 mM IPTG or 2% lactose (both in final concentration) to each cell culture medium, expression of recombinant $E.\ coli$ was induced. After gene expression induction, the cells were further cultured for 3 to 4 hours, and then collected by centrifuge. The collected cells were sufficiently suspended in a buffer solution (phosphate buffered saline, 8 g of sodium chloride, 0.2 g of potassium chloride, 1.44 g of sodium hydrogen phosphate ($Na_2HPO_4$), and 0.24 g of potassium dihydrogen phohsphate ($KH_2PO_4$)£, pH 7.4) and disrupted using an ultrasonic cell homogenizer. As a result, a solution containing intracellular proteins was separated.

By using the above separated solution as a sample, protein expression was examined by 15% SDS-polyacrylamide gel electrophoresis. As a result, expression of the human epidermal growth factor-spider venom fusion protein was confirmed from crude cell lysate in which the expression induction has been carried out with IPTG or lactose (FIG. 2A).

In order to isolate and purify the human epidermal growth factor-spider venom fusion protein of which expression has been confirmed from above, the inclusion body was solubilized using a solubilizing buffer solution (5M urea, pH 11), and then subjected to a refolding process using ultrafine filtration (0.45 μm fine filtration membrane, and 1K ultrafine filtration membrane). Accordingly, the human epidermal growth factor-spider venom fusion protein was finally isolated by using a storage buffer solution (PBS).

Figure 2B:
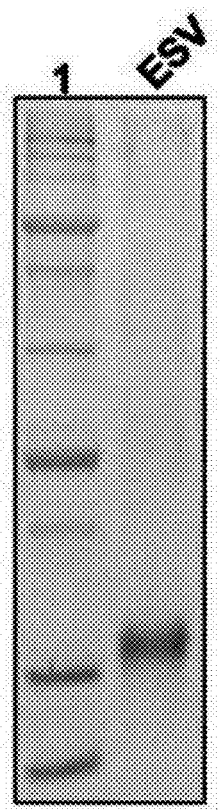
Figure 2C:
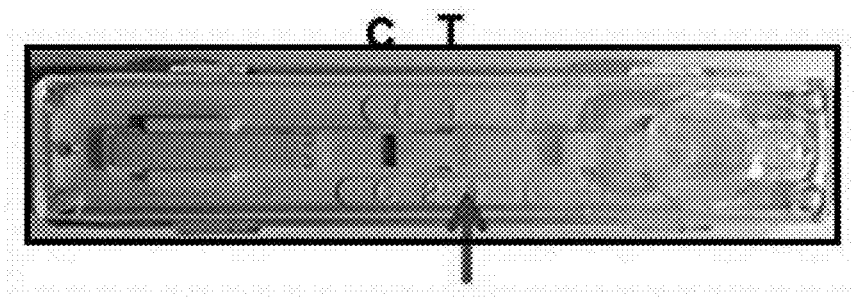

For complete purification of the above fusion protein, the isolated fusion protein was passed through a nickel-agarose column at a rate of 1 to 3 ml/minute. Subsequently, the column was washed several times with a binding buffer solution, and by adding 50, 1000, and 250 mM imidazole solution (pH 7.4) to the column, the human epidermal growth factor-spider venom fusion protein was fractionated in a portion of 1 ml and eluted from the column. Then, the imidazole present in the buffer was removed by using 10 mM potassium phosphate buffer, and thus the fusion protein was finally purified in pure state. To determine the result, 15% SDS-acrylamide gel electrophoresis was carried out. As a result, the finally purified fusion protein was confirmed with near expected size (i.e., about 14 to 16 kDa, including His tag) (FIG. 2B). Finally, by using an EGF detection kit, the EGF domain in the human epidermal growth factor-spider venom fusion protein was confirmed (FIG. 2C).

Example 3. Measurement of Activity of Human Epidermal Growth Factor-Spider Venom Fusion Protein—Dermal Fibroblast Proliferation Effect With selection of a sample from which the presence of isolated and purified human epidermal growth factor-spider venom fusion protein has been confirmed as described in Example 2, an activity of the human epidermal growth factor-spider venom fusion protein was measured.

After culturing dermal fibroblast (Human Dermal Fibroblasts adult, HDFa cell), the cells were treated with the fusion protein at concentration of 0, 0.02 ppm, or 0.2 ppm followed by culture for 3 days at 37° C. Thereafter, proliferation of the dermal fibroblast was determined based on crystal violet staining.

Figure 3:
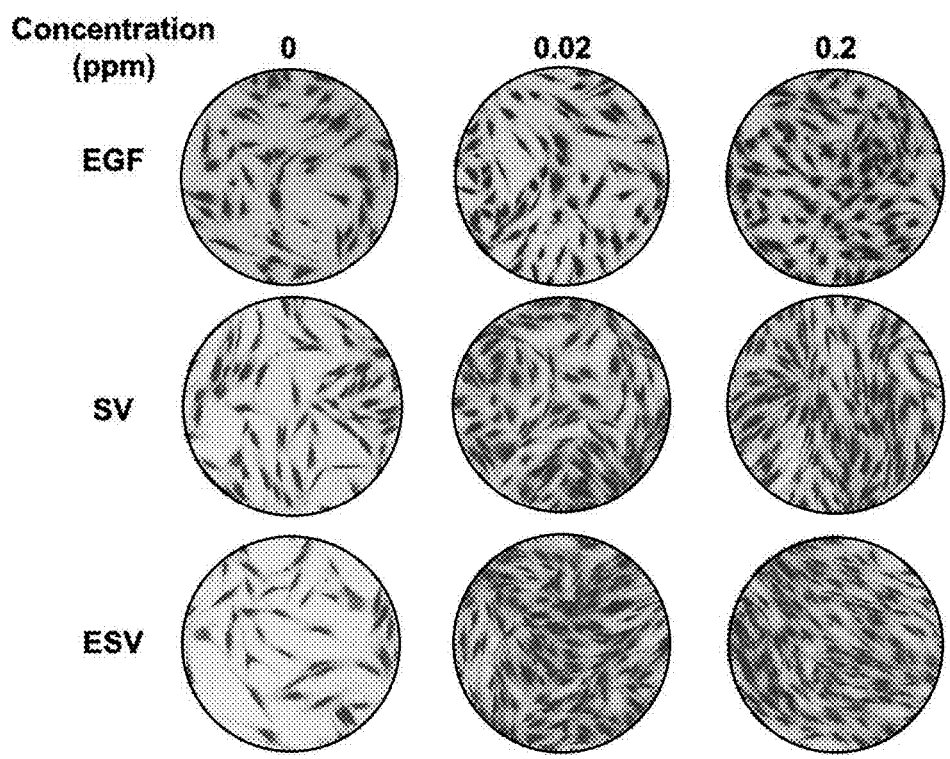

As a result, it was found that, compared to a non-treatment control group (0 ppm), a more favorable dermal fibroblast proliferation effect is obtained as the concentration of the human epidermal growth factor-spider venom fusion protein increases (0.02 to 0.2 ppm) (FIG. 3). Furthermore, compared to each of single protein treatment group (EGV and SV), higher cell proliferation effect was observed with the human epidermal growth factor-spider venom fusion protein (ESV). This result indicates that each of EGF and SV in the fusion protein does not correspond to a full-length protein but corresponds to each active domain used for production of the human epidermal growth factor-spider venom fusion protein, and when the treatment is carried out using each protein or the human epidermal growth factor-spider venom fusion protein (ESV) at the same concentration (for example, 0.02 ppm), mole number of the human epidermal growth factor-spider venom fusion protein (ESV) is approximately ½ of EGF and SV, respectively. Thus, if a similar dermal fibroblast proliferation is exhibited at the same concentration, it is believed that the human epidermal growth factor-spider venom fusion protein has the dermal fibroblast proliferation effect that is almost 2 times higher than EGF and SV, respectively. As shown in FIG. 3, compared to EGF and SV, there is a higher number of dermal fibroblast when it is treated with human epidermal growth factor-spider venom fusion protein, indicating the dermal fibroblast proliferation effect that is almost 2 times higher than EGF and SV, respectively. Based on the above results, it is believed that the human epidermal growth factor-spider venom fusion protein has an enhanced skin cell proliferation effect.

Example 4. Thermostability Analysis of Human Epidermal Growth Factor-Spider Venom Fusion Protein With selection of a sample from which the presence of isolated and purified human epidermal growth factor-spider venom fusion protein has been confirmed as described in Example 2, a thermostability test was carried out. For the thermostability test, dermal fibroblast was treated with the human epidermal growth factor-spider venom fusion protein at a concentration of 0.02 to 0.2 ppm, which has been subjected to either gamma sterilization (irradiation of 35 kgray) or high pressure sterilization (treatment at 121° C. for 15 minutes), followed by culture for 3 days at 37° C. Then, cell proliferation degree depending on the protein treatment was determined based on crystal violet staining.

Figure 4:
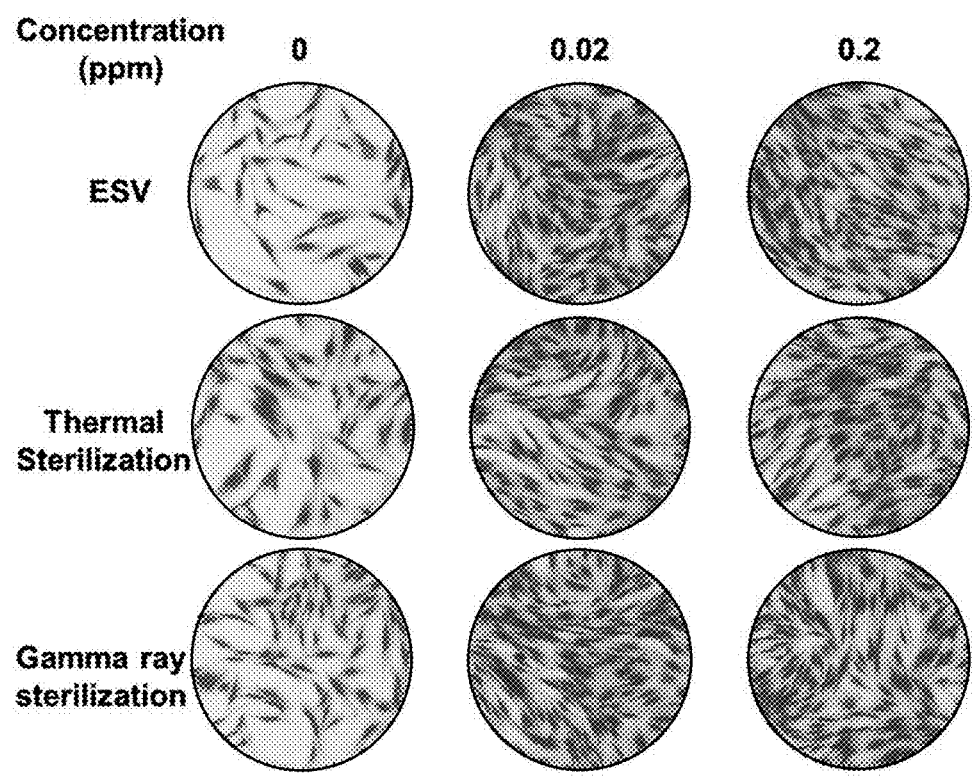

As a result, it was found that the cell proliferation caused by the human epidermal growth factor-spider venom fusion protein in the gamma sterilization group or the high pressure sterilization group was similar to the cell proliferation of a group without any heating treatment (FIG. 4).

Based on the above result, it was found that the human epidermal growth factor-spider venom fusion protein of the present invention maintains the protein activity even after a heating treatment, and the human epidermal growth factor-spider venom fusion protein of the present invention with enhanced skin cell proliferation effect is believed to be very advantageously used for production of a preservative-free cosmetic product which is produced by using a heating treatment method.

Example 5. Measurement of Activity of Human Epidermal Growth Factor-Spider Venom Fusion Protein—Cell Proliferation, Wound Healing, and Cell Adhesion Effect in HaCaT Cells With selection of a sample from which the presence of isolated and purified human epidermal growth factor-spider venom fusion protein has been confirmed as described in Example 2, activity of the human epidermal growth factor-spider venom fusion protein was measured. The measurement of the activity of fusion protein was carried out by culturing HaCaT cells, treating the cultured cells with the fusion protein at a concentration of 0, 0.02 ppm, 0.2 ppm, 2 ppm, and 20 ppm, and analyzing the cell proliferation, wound healing, and cell adhesion in the cultured cells.

Figure 5:
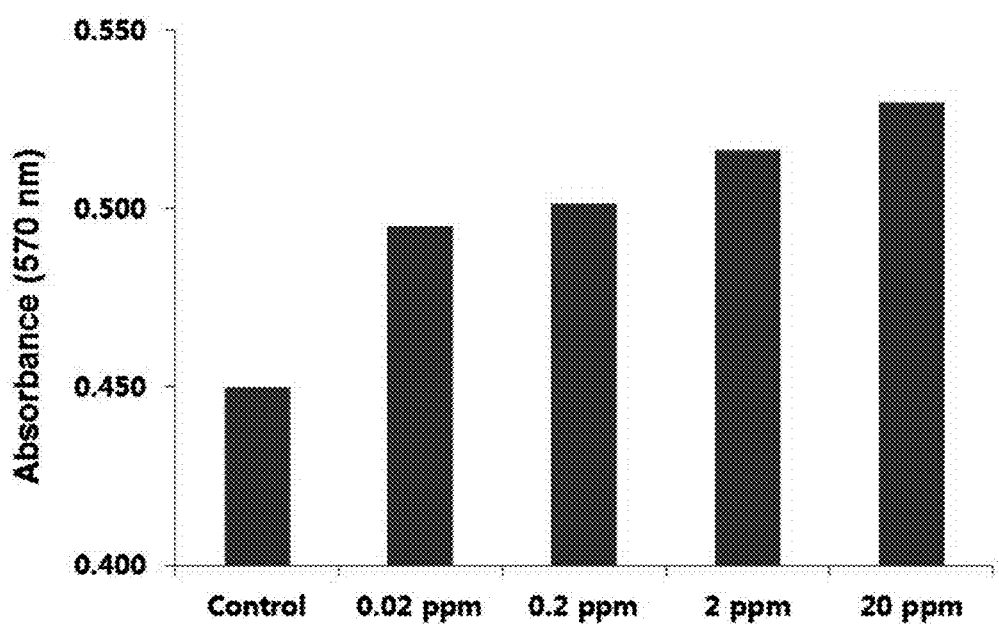

First, when cell proliferation analysis was made by using PRESTOBLUE™ Cell Viability reagent (Invitrogen, USA), HaCaT cell proliferation effect caused by a treatment of the human epidermal growth factor-spider venom fusion protein was confirmed. Furthermore, as the concentration of the human epidermal growth factor-spider venom fusion protein increases (0.02 to 20 ppm), more favorable cell proliferation effect was observed (FIG. 5).

Figure 6:
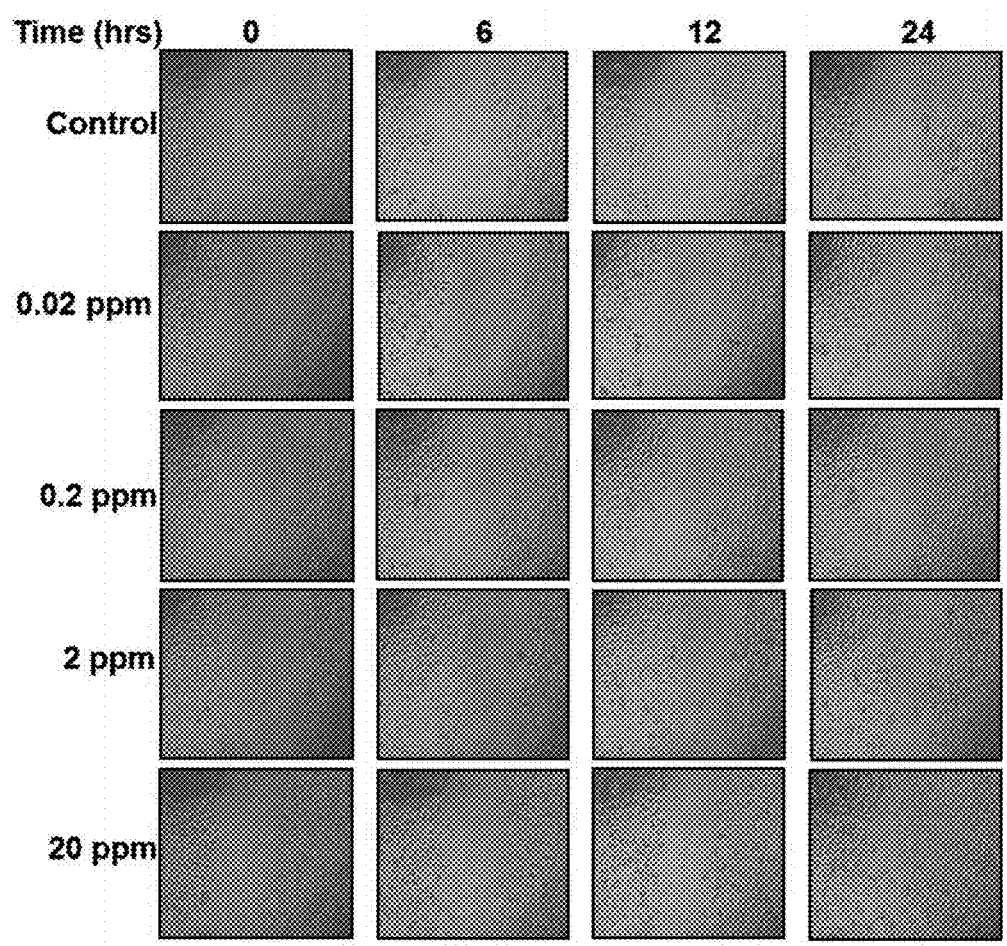

After culturing HaCaT cells in a well, the human epidermal growth factor-spider venom fusion protein was added thereto at a concentration of 0, 0.02 ppm, 0.2 ppm, 2 ppm, and 20 ppm. Thereafter, the cells were observed every 6 hours by a microscope (Olympus CK40, Olympus, Japan) to examine the wound healing effect in HaCaT cells. When compared to a non-treatment control group (i.e., no treatment with human epidermal growth factor-spider venom fusion protein), the HaCaT cells treated with the human epidermal growth factor-spider venom fusion protein showed a wound healing effect, and it was particularly shown that the effect is stronger as the concentration of the human epidermal growth factor-spider venom fusion protein increases (0.02 to 20 ppm) (FIG. 6).

Figure 7:
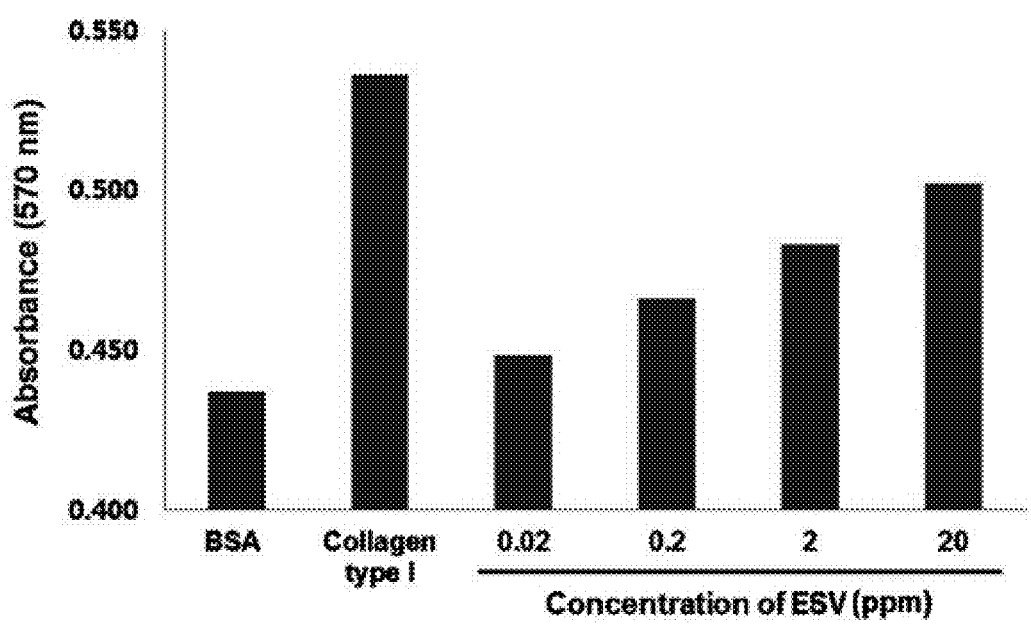

As a last step, the human epidermal growth factor-spider venom fusion protein with a concentration of 0, 0.02 ppm, 0.2 ppm, 2 ppm, and 20 ppm was coated on a 96-well plate, which was then treated with HaCaT cells followed by culture for 1 day at 37° C. After that, by using PRESTOBLUE™ Cell Viability reagent, the adhesion effect between the cells and human epidermal growth factor-spider venom fusion protein was analyzed. As a result, it was shown that the HaCaT cells treated with the human epidermal growth factor-spider venom fusion protein exhibited higher adhesion effect compared to the negative control group which has been treated with BSA (bovine serum albumin). Thus, the adhesion effect of the human epidermal growth factor-spider venom fusion protein onto a skin cell was confirmed (FIG. 7).

Test Example 1. Skin Wrinkle Improvement, Skin Elasticity Maintaining Effect, and Skin Irritation Sensory Test By using the human epidermal growth factor-spider venom fusion protein which has been isolated and purified as described in Example 2 as an effective component, cosmetic compositions of Preparation examples 1, 2, 3 and 4 and Comparative examples 1, 2, 3 and 4 were prepared and used for a sensory test.

Specifically, to confirm any wrinkle improvement, total 30 men and women with age of 30 or higher but lower than 60 (10 in 30's. 10 in 40's, and 10 in 50's and 60's) as a subject were allowed to apply, once a day for 2 weeks continuously, the composition of Comparative example (i.e., control group) around an eye area at left side of a face or around left side of lips in which many wrinkles are found, or the composition of Preparation example (i.e., test group) around an eye area at right side of a face or around right side of lips. The evaluation was made based on wrinkle reduction level around the eye or lips. Furthermore, also for the skin elasticity maintaining effect as one of the functional item described above, the skin elasticity maintaining degree was evaluated according to the same method as described above. Also for the skin irritation item, a sensory test was carried out according to the same method as described above in terms of itchiness, stingy feeling, and an erythema phenomenon. The evaluation was made based on five-point evaluation criteria, i.e., very excellent (5 points), excellent (4 points), moderate (3 points), poor (2 points), and very poor (1 point).

Preparation Example 1 and Comparative Example 1

By adding the human epidermal growth factor-spider venom fusion protein as an effective component and having the components and content that are described in the following Table 1, a skin of Preparation example 1 was prepared.

Furthermore, without adding the human epidermal growth factor-spider venom fusion protein as an effective component but having the components and content that are described in the following Table 1, a skin of Comparative example 1 was prepared.

TABLE 1

Skin composition

| Component | Preparation example 1 (% by weight) | Comparative example 1 (% by weight) |
|---|---|---|
| Human epidermal growth factor-spider venom fusion protein | 0.01 | — |
| Amino acid stock | 0.1 | 0.1 |
| Mineral mixture | 0.0007 | 0.0007 |
| Purified water | q.s. | q.s. |

The sensory test results of above Preparation example 1 and Comparative example 1 are as shown in the following Table 2.

TABLE 2

Sensory test result of Preparation example 1 and Comparative example 1

Sensory test regarding wrinkle improvement and skin elasticity maintaining effect

| | No. | Wrinkle improvement | | Skin elasticity maintaining-effect | | Skin irritation Preparation example |
|---|---|---|---|---|---|---|
| | | Preparation example | Comparative example | Preparation example | Comparative example | |
| 30's | 1 | 4 | 3 | 5 | 3 | 4 |
| | 2 | 4 | 3 | 4 | 3 | 5 |
| | 3 | 4 | 3 | 4 | 3 | 4 |
| | 4 | 4 | 3 | 3 | 3 | 4 |
| | 5 | 4 | 2 | 4 | 2 | 4 |
| | 6 | 4 | 2 | 4 | 3 | 4 |
| | 7 | 4 | 3 | 5 | 3 | 4 |
| | 8 | 4 | 2 | 4 | 3 | 4 |
| | 9 | 4 | 2 | 4 | 3 | 5 |
| | 10 | 3 | 3 | 4 | 3 | 4 |
| 40's | 11 | 4 | 2 | 5 | 3 | 4 |
| | 12 | 4 | 2 | 5 | 2 | 4 |
| | 13 | 4 | 2 | 4 | 3 | 5 |
| | 14 | 5 | 3 | 5 | 2 | 5 |
| | 15 | 5 | 2 | 4 | 2 | 5 |
| | 16 | 4 | 3 | 4 | 2 | 4 |
| | 17 | 5 | 2 | 5 | 2 | 5 |
| | 18 | 4 | 3 | 5 | 3 | 5 |
| | 19 | 5 | 3 | 4 | 3 | 5 |
| | 20 | 4 | 3 | 5 | 2 | 4 |
| 50's and 60's | 21 | 5 | 2 | 4 | 3 | 5 |
| | 22 | 5 | 2 | 4 | 2 | 5 |
| | 23 | 5 | 2 | 5 | 2 | 5 |
| | 24 | 4 | 3 | 4 | 2 | 5 |
| | 25 | 3 | 2 | 5 | 2 | 4 |
| | 26 | 5 | 3 | 4 | 2 | 4 |
| | 27 | 5 | 2 | 5 | 3 | 5 |
| | 28 | 5 | 2 | 4 | 2 | 5 |
| | 29 | 4 | 2 | 5 | 3 | 5 |
| | 30 | 4 | 2 | 5 | 2 | 4 |
| Average | | 4.2 | 2.4 | 4.4 | 2.5 | 4.5 |

Preparation Example 2 and Comparative Example 2

By adding the human epidermal growth factor-spider venom fusion protein as an effective component and having the components and content that are described in the following Table 3, an essence of Preparation example 2 was prepared.

Furthermore, without adding the human epidermal growth factor-spider venom fusion protein as an effective component but having the components and content that are described in the following Table 3, an essence of Comparative example 2 was prepared.

TABLE 3

Essence composition

| Component | Preparation example 2 (% by weight) | Comparative example 2 (% by weight) |
|---|---|---|
| Human epidermal growth factor-spider venom fusion protein | 0.01 | — |
| Amino acid stock | 0.05 | 0.05 |
| Mineral mixture | 0.0007 | 0.0007 |
| Glycerol | 5 | 5 |
| 1,3-Butylene glycol | 10 | 10 |
| Carbopol 940 | 0.3 | 0.3 |
| Purified water | q.s. | q.s. |

The sensory test results of above Preparation example 2 and Comparative example 2 are as shown in the following Table 4.

TABLE 4

Sensory test result of Preparation example 2 and Comparative example 2

Sensory test regarding wrinkle improvement and skin elasticity maintaining effect

| No. | | Wrinkle improvement | | Skin elasticity maintaining-effect | | Skin irritation Preparation example |
|---|---|---|---|---|---|---|
| | | Preparation example | Comparative example | Preparation example | Comparative example | |
| 30's | 1 | 4 | 3 | 5 | 3 | 4 |
| | 2 | 4 | 2 | 4 | 3 | 5 |
| | 3 | 4 | 3 | 4 | 3 | 4 |
| | 4 | 5 | 3 | 4 | 3 | 4 |
| | 5 | 4 | 2 | 3 | 3 | 4 |
| | 6 | 5 | 3 | 4 | 3 | 4 |
| | 7 | 4 | 3 | 4 | 3 | 4 |
| | 8 | 5 | 2 | 5 | 3 | 4 |
| | 9 | 4 | 3 | 5 | 2 | 5 |
| | 10 | 4 | 3 | 4 | 3 | 4 |
| 40's | 11 | 5 | 3 | 5 | 3 | 5 |
| | 12 | 4 | 3 | 4 | 2 | 5 |
| | 13 | 4 | 2 | 5 | 3 | 5 |
| | 14 | 5 | 3 | 5 | 3 | 5 |
| | 15 | 5 | 2 | 5 | 3 | 5 |
| | 16 | 5 | 2 | 4 | 2 | 4 |
| | 17 | 5 | 3 | 5 | 3 | 5 |
| | 18 | 4 | 3 | 5 | 3 | 5 |
| | 19 | 5 | 3 | 4 | 3 | 5 |
| | 20 | 4 | 3 | 5 | 2 | 5 |
| 50's and 60's | 21 | 5 | 3 | 4 | 3 | 5 |
| | 22 | 5 | 3 | 5 | 4 | 5 |
| | 23 | 5 | 2 | 5 | 3 | 5 |
| | 24 | 4 | 3 | 5 | 3 | 5 |
| | 25 | 5 | 2 | 4 | 3 | 5 |
| | 26 | 5 | 3 | 5 | 2 | 4 |
| | 27 | 5 | 3 | 5 | 3 | 5 |
| | 28 | 5 | 3 | 4 | 3 | 5 |
| | 29 | 4 | 3 | 5 | 3 | 5 |
| | 30 | 5 | 4 | 5 | 3 | 4 |
| Average | | 4.6 | 2.8 | 4.5 | 2.9 | 4.6 |

Preparation Example 3 and Comparative Example 3

By adding the human epidermal growth factor-spider venom fusion protein as an effective component and having the components and content that are described in the following Table 5, a lotion of Preparation example 3 was prepared.

Furthermore, without adding the human epidermal growth factor-spider venom fusion protein as an effective component but having the components and content that are described in the following Table 5, a lotion of Comparative example 3 was prepared.

TABLE 5

Lotion composition

| Component | Preparation example 3 (% by weight) | Comparative example 3 (% by weight) |
|---|---|---|
| Human epidermal growth factor-spider venom fusion protein | 0.01 | — |
| Amino acid stock | 0.05 | 0.05 |
| Mineral mixture | 0.0007 | 0.0007 |
| Glycerol | 3 | 3 |
| 1,3-Butylene glycol | 10 | 10 |
| Mineral oil | 5 | 5 |
| Cetyl alcohol | 2 | 2 |
| Xanthan gum | 0.5 | 0.5 |
| Purified water | q.s. | q.s. |

The sensory test results of above Preparation example 3 and Comparative example 3 are as shown in the following Table 6.

TABLE 6

Sensory test result of Preparation example 3 and Comparative example 3

Sensory test regarding wrinkle improvement and skin elasticity maintaining effect

| No. | | Wrinkle improvement | | Skin elasticity maintaining-effect | | Skin irritation Preparation example |
|---|---|---|---|---|---|---|
| | | Preparation example | Comparative example | Preparation example | Comparative example | |
| 30's | 1 | 4 | 3 | 5 | 3 | 5 |
| | 2 | 4 | 3 | 3 | 4 | 5 |
| | 3 | 4 | 3 | 3 | 3 | 4 |
| | 4 | 3 | 3 | 3 | 3 | 4 |
| | 5 | 4 | 2 | 3 | 3 | 4 |
| | 6 | 3 | 2 | 3 | 2 | 5 |
| | 7 | 4 | 3 | 4 | 3 | 5 |
| | 8 | 4 | 3 | 4 | 3 | 4 |
| | 9 | 4 | 3 | 5 | 4 | 5 |
| | 10 | 4 | 3 | 3 | 3 | 4 |
| 40's | 11 | 5 | 3 | 5 | 3 | 5 |
| | 12 | 5 | 4 | 5 | 3 | 5 |
| | 13 | 5 | 3 | 5 | 2 | 5 |
| | 14 | 5 | 3 | 5 | 2 | 5 |
| | 15 | 5 | 3 | 5 | 3 | 5 |
| | 16 | 5 | 3 | 4 | 2 | 4 |
| | 17 | 5 | 4 | 5 | 3 | 5 |
| | 18 | 5 | 3 | 5 | 3 | 5 |
| | 19 | 5 | 3 | 5 | 1 | 5 |
| | 20 | 5 | 3 | 5 | 2 | 5 |
| 50's and 60's | 21 | 5 | 3 | 5 | 3 | 5 |
| | 22 | 5 | 3 | 5 | 2 | 5 |
| | 23 | 5 | 2 | 4 | 3 | 5 |
| | 24 | 4 | 2 | 4 | 2 | 5 |
| | 25 | 4 | 3 | 5 | 3 | 5 |
| | 26 | 5 | 3 | 4 | 2 | 4 |
| | 27 | 4 | 2 | 5 | 3 | 5 |
| | 28 | 5 | 3 | 5 | 3 | 5 |
| | 29 | 5 | 2 | 4 | 3 | 5 |
| | 30 | 5 | 3 | 5 | 3 | 5 |
| Average | | 4.5 | 2.9 | 4.4 | 2.7 | 4.8 |

Preparation Example 4 and Comparative Example 4

By adding the human epidermal growth factor-spider venom fusion protein as an effective component and having the components and content that are described in the following Table 7, a crème of Preparation example 4 was prepared.

Furthermore, without adding the human epidermal growth factor-spider venom fusion protein as an effective component but having the components and content that are described in the following Table 7, a crème of Comparative example 4 was prepared.

TABLE 7

Crème composition

| Component | Preparation example 4 (% by weight) | Comparative example 4 (% by weight) |
|---|---|---|
| Human epidermal growth factor-spider venom fusion protein | 0.01 | — |
| Amino acid stock | 0.05 | 0.05 |
| Mineral mixture | 0.0007 | 0.0007 |
| Glycerol | 2 | 2 |
| Mineral oil | 10 | 10 |
| Olive emulsion wax | 3 | 3 |
| Cetyl alcohol | 2 | 2 |
| Purified water | q.s. | q.s. |

The sensory test results of above Preparation example 4 and Comparative example 4 are as shown in the following Table 8.

TABLE 8

Sensory test result of Preparation example 4 and Comparative example 4

Sensory test regarding wrinkle improvement and skin elasticity maintaining effect

| | No. | Wrinkle improvement | | Skin elasticity maintaining-effect | | Skin irritation Preparation example |
|---|---|---|---|---|---|---|
| | | Preparation example | Comparative example | Preparation example | Comparative example | |
| 30's | 1 | 4 | 3 | 4 | 3 | 5 |
| | 2 | 4 | 3 | 4 | 2 | 5 |
| | 3 | 3 | 3 | 4 | 3 | 4 |
| | 4 | 4 | 3 | 5 | 3 | 4 |
| | 5 | 4 | 3 | 4 | 3 | 5 |
| | 6 | 4 | 2 | 3 | 2 | 4 |
| | 7 | 4 | 3 | 4 | 3 | 5 |
| | 8 | 3 | 3 | 5 | 3 | 4 |
| 40's | 9 | 5 | 3 | 3 | 2 | 5 |
| | 10 | 4 | 3 | 4 | 3 | 4 |
| | 11 | 5 | 3 | 5 | 3 | 5 |
| | 12 | 4 | 3 | 5 | 3 | 5 |
| | 13 | 5 | 2 | 4 | 2 | 5 |
| | 14 | 4 | 3 | 3 | 2 | 5 |
| | 15 | 5 | 2 | 5 | 3 | 5 |
| | 16 | 5 | 3 | 3 | 2 | 4 |
| | 17 | 4 | 2 | 4 | 3 | 5 |
| | 18 | 4 | 3 | 4 | 3 | 4 |
| | 19 | 5 | 3 | 5 | 2 | 5 |
| | 20 | 4 | 2 | 4 | 2 | 5 |
| 50's and 60's | 21 | 5 | 3 | 4 | 3 | 5 |
| | 22 | 5 | 3 | 4 | 2 | 4 |
| | 23 | 4 | 2 | 5 | 3 | 5 |
| | 24 | 4 | 3 | 4 | 2 | 5 |
| | 25 | 4 | 2 | 4 | 2 | 5 |
| | 26 | 4 | 3 | 5 | 3 | 4 |
| | 27 | 4 | 3 | 4 | 3 | 5 |
| | 28 | 3 | 2 | 5 | 3 | 4 |
| | 29 | 4 | 3 | 4 | 3 | 5 |
| | 30 | 4 | 3 | 4 | 2 | 4 |
| Average | | 4.2 | 2.7 | 4.2 | 2.6 | 4.6 |

From the sensory test results that are given above, it was found that, compared to Comparative examples, Preparation examples 1, 2, 3 and 4 in which the human epidermal growth factor-spider venom fusion protein of the present invention is contained as an effective component are effective for improvement of skin wrinkle and maintaining of skin elasticity.

The invention claimed is:

1. A thermostable human epidermal growth factor-spider venom fusion protein with increased skin cell proliferation effect, the protein consisting of the amino acid sequence of SEQ ID NO: 2.

2. A cosmetic composition for improving skin wrinkle and maintaining skin elasticity comprising, as an effective component, a thermostable human epidermal growth factor-spider venom fusion protein with increased skin cell proliferation effect, the protein consisting of the amino acid sequence of SEQ ID NO: 2.

3. A gene encoding the thermostable human epidermal growth factor-spider venom fusion protein of claim 1.

4. The gene of claim 3, wherein the gene consists of Escherichia coli (E. coli) codon-optimized nucleotide sequence of SEQ ID NO: 1.

5. A recombinant vector comprising the gene of claim 3.

6. An isolated host cell transformed with the recombinant vector of claim 5.

7. A method for producing in a host cell a human epidermal growth factor-spider venom fusion protein, the method comprising transforming the host cell with the recombinant vector of claim 5, and expressing the gene encoding the thermostable human epidermal growth factor-spider venom fusion protein.

8. The method for producing a human epidermal growth factor-spider venom fusion protein of claim 7, wherein the host cell is E. coli.

9. A recombinant vector comprising the gene of claim 4.

10. An isolated host cell transformed with the recombinant vector of claim 9.

11. A method for producing in a host cell a human epidermal growth factor-spider venom fusion protein, the method comprising transforming the host cell with the recombinant vector of claim 9, and expressing the gene encoding the thermostable human epidermal growth factor-spider venom fusion protein.

12. The method for producing a human epidermal growth factor-spider venom fusion protein of claim 11, wherein the host cell is E. coli.

* * * * *

SEQUENCE LISTING

<160> NUMBER OF SEQ ID NOS: 6

<210> SEQ ID NO 1
<211> LENGTH: 309
<212> TYPE: DNA
<213> ORGANISM: Artificial Sequence
<220> FEATURE:
<223> OTHER INFORMATION: EGF-SV

<400> SEQUENCE: 1

```
aactcagact ctgagtgccc actgtctcac gacggctact gccttcacga cggagtctgc    60
atgtacatcg aggctttgga taagtacgct tgtaattgcg tcgttggtta cattggagag   120
cgctgccaat accgtgactt aaaatggtgg gagttgcgcg ccagggctac ctgtgcaggg   180
caggatcagc catgcaaaga aacgtgcgat tgctgtggcg aacgtggcga atgcgtgtgt   240
ggtggtccgt gcatttgtcg ccaaggctat ttctggattg cgtggtacaa actggcgaac   300
tgcaagaaa                                                           309
```

<210> SEQ ID NO 2
<211> LENGTH: 103
<212> TYPE: PRT
<213> ORGANISM: Artificial Sequence

<220> FEATURE:
<223> OTHER INFORMATION: EGF-SV

<400> SEQUENCE: 2

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Ala Arg Ala Thr Cys Ala Gly Gln Asp Gln Pro
    50                  55                  60

Cys Lys Glu Thr Cys Asp Cys Cys Gly Glu Arg Gly Glu Cys Val Cys
65              70                  75                  80

Gly Gly Pro Cys Ile Cys Arg Gln Gly Tyr Phe Trp Ile Ala Trp Tyr
            85                  90                  95

Lys Leu Ala Asn Cys Lys Lys
            100

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
aaggagatat acatatgaac tcagac                                          26

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
agccctggcg cgcaactc                                                   18

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
gagttgcgcg ccagggct                                                   18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
gtgctcgagt ttcttgca                                                   18